(12) United States Patent
Andjelic et al.

(10) Patent No.: US 8,575,301 B2
(45) Date of Patent: Nov. 5, 2013

(54) ABSORBABLE POLYMER FORMULATIONS

(71) Applicant: Ethicon, Inc., Somerville, NJ (US)

(72) Inventors: Sasa Andjelic, Nanuet, NY (US); Tara Zabrosky, Millstone Township, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/691,434

(22) Filed: Nov. 30, 2012

(65) Prior Publication Data

US 2013/0089511 A1    Apr. 11, 2013

Related U.S. Application Data

(60) Division of application No. 11/864,153, filed on Sep. 28, 2007, which is a continuation-in-part of application No. 10/934,066, filed on Sep. 3, 2004, now Pat. No. 7,754,233.

(51) Int. Cl.
*C08G 63/08* (2006.01)

(52) U.S. Cl.
USPC .......... 528/318; 424/423; 525/386; 525/415; 525/437; 528/310; 528/354

(58) Field of Classification Search
USPC .......... 424/423; 525/386, 415, 437; 528/310, 528/318, 354
See application file for complete search history.

(56) References Cited

U.S. PATENT DOCUMENTS

| | | | |
|---|---|---|---|
| 3,997,512 A | 12/1976 | Casey et al. | |
| 4,048,256 A | 9/1977 | Casey et al. | |
| 4,076,798 A | 2/1978 | Casey et al. | |
| 4,095,600 A | 6/1978 | Casey et al. | |
| 4,118,470 A | 10/1978 | Casey et al. | |
| 4,122,129 A | 10/1978 | Casey et al. | |
| 4,938,763 A | 7/1990 | Dunn et al. | |
| 5,442,033 A | 8/1995 | Bezwada | |
| 5,464,929 A | 11/1995 | Bezwada et al. | |
| 5,599,852 A | 2/1997 | Scopelianos et al. | |
| 5,618,552 A | 4/1997 | Bezwada et al. | |
| 5,644,002 A | 7/1997 | Cooper et al. | |
| 5,653,992 A | 8/1997 | Bezwada et al. | |
| 5,688,900 A | 11/1997 | Cooper et al. | |
| 5,696,178 A * | 12/1997 | Cooper et al. | 522/43 |
| 5,728,752 A | 3/1998 | Scopelianos et al. | |
| 5,736,589 A | 4/1998 | Cooper et al. | |
| 5,824,333 A | 10/1998 | Scopelianos et al. | |
| 6,147,168 A | 11/2000 | Jamiolkowski et al. | |
| 6,224,894 B1 | 5/2001 | Jamiolkowski et al. | |
| 6,403,655 B1 | 6/2002 | Bezwada et al. | |
| 6,716,251 B1 | 4/2004 | Asius et al. | |
| 2006/0051398 A1 | 3/2006 | Andjelic et al. | |
| 2006/0263329 A1 | 11/2006 | Eemeta et al. | |
| 2009/0239786 A1 | 9/2009 | Stopek | |

FOREIGN PATENT DOCUMENTS

WO     2008/055086     5/2008

OTHER PUBLICATIONS

Andjelic, S., et al 'Hydrophilic Absorbable Copolyester Exhibiting Zero-Order Drug Release' Pharmaceutical Research (2006) vol. 23, Issue 4 pp. 821-834.
Andjelic, S., et al 'The Polyoxaesters' Polymer International (2007) vol. 56, Issue 9 pp. 1063-1077.
C.B. Packhaeuser et al., "In situ forming parenteral drug delivery systems: an overview", European Journal of Pharmaceutics and Biopharmaceutics 58, (2004) 445-455.

* cited by examiner

*Primary Examiner* — Gregory Listvoyb
(74) *Attorney, Agent, or Firm* — David R. Crichton

(57) ABSTRACT

A co-polyester which includes the reaction product of a polycondensation polyester and epsilon-caprolactone, wherein the polycondensation polyester comprises the reaction product of diglycolic acid and/or a derivative thereof and a diol. The co-polyester is injectable and absorbable into animal, such as human, tissue and can be used for facial cosmetic or reconstructive surgery of soft tissue. Another embodiment is directed to a method for preventing adhesion using a co-polyester comprising the reaction product of a polycondensation polyester and epsilon-caprolactone, wherein the polycondensation polyester comprises the reaction product of diglycolic acid and/or a derivative thereof and a diol, and the co-polyester comprises about 40 to 50% by weight of the polycondensation polyester based on the total weight of the co-polyester.

9 Claims, 1 Drawing Sheet

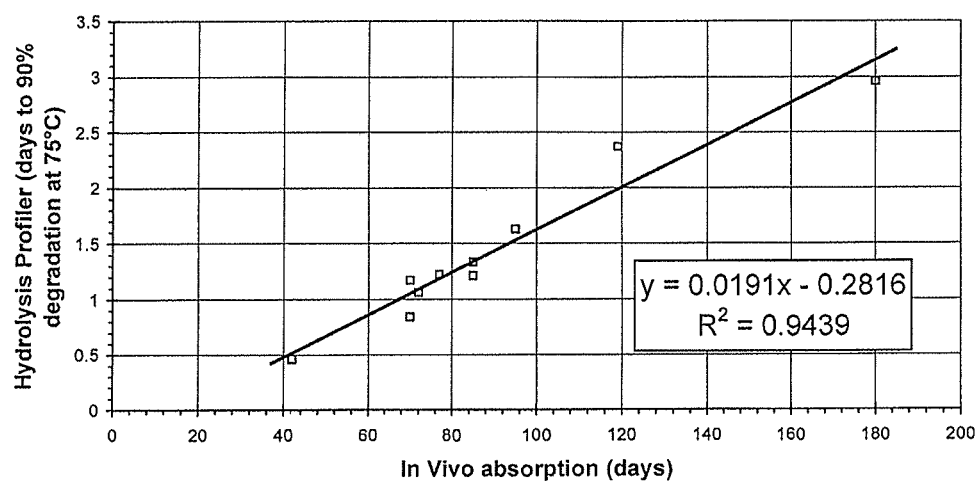
Correlation between Hydrolysis Profiler & *In Vivo* Data

ABSORBABLE POLYMER FORMULATIONS

CROSS-REFERENCE TO RELATED APPLICATIONS

This application is a Divisional of U.S. patent application Ser. No. 11/864,153, filed on Sep. 28, 2007, which is a continuation-in-part of U.S. patent application Ser. No. 10/934,066, filed on Sep. 3, 2004, now U.S. Pat. No. 7,754,233, the entire contents of each are incorporated herein by reference.

FIELD OF THE INVENTION

The invention relates to injectable, absorbable polymer formulations for plastic and reconstructive surgery applications, and methods of using thereof with an absorbable co-polyester of a condensation polyester and epsilon-caprolactone. The invention also relates to a method of preventing adhesions using absorbable co-polyester of a polycondensation polyester and at least one lactone.

BACKGROUND OF THE INVENTION

The repair or augmentation of soft tissue, such as soft tissue defects, or contour abnormalities caused by a variety of factors, such as facial defects, acne, surgical scarring or aging, accidents or purely for cosmetic reasons, has proven to be challenging. A number of materials have been used to correct soft tissue defects or augment soft tissue, with varying degrees of success. In the past, liquid silicone was used to correct minor soft tissue defects where minimal mechanical stress was present at the recipient's site. Unfortunately, it appears that liquid silicone from these injections may migrate to distant body parts and cause a variety of physiological and clinical problems. In response to these problems and the misuse of liquid silicone, the FDA at times prohibited the use of liquid silicone in humans.

In the 1970's, reconstituted injectable bovine collagen became available and appeared to be an effective treatment for soft tissue defects. However, over time, the benefits of the collagen treatment have proven to be short-lived; the collagen reabsorbs in two to three months. Additionally, safety measures must be employed with this material to avoid allergic reactions to the bovine proteins in the collagen. To solve these shortcomings, crosslinked collagen has been introduced to extend the effect of treatments to approximately six (6) months. However, allergic reactions may still occur with the cross-linked collagen material and frequent re-administration of the cross-linked material is still required.

U.S. Pat. No. 6,716,251, assigned to Aventis Pharmaceuticals Holdings, Inc., describes the use of an injection implant for filling up wrinkles, thin lines, skin cracks and scars, for reparative or plastic surgery, aesthetic dermatology, and for filling up gums in dental treatment. The implant includes biologically absorbable polymer microspheres or microparticles suspended in a gel. Two polymer families are described as being suitable, the polycaprolactones (and in particular the poly-epsilon-caprolactones), as well as the polylactides (polylactic acids or PLA), the poly-glycolides (polyglycolic acids or PGA) and their copolymers (polylactic-co-glycolic acids or PLAGA).

U.S. Pat. No. 4,938,763, assigned to Atrix Laboratories, Inc., discloses the use of biodegradable polymers as prosthetic implants and controlled-release, drug-delivery systems which can be administered as liquids via, for example, a syringe and needle, but which coagulate or cure shortly after dosing to form a solid. The implants are biodegradable because they are made from biodegradable polymers and copolymers comprising two types of polymer systems: thermoplastic and thermosetting. Examples of thermoplastic systems are polylactides, polyglycolides, polycaprolactones, and polyamides, preferably polylactides, polycaprolactones, and copolymers thereof with glycolide in which there are more amorphous regions to enhance solubility. The polymers used in the thermosetting system are multifunctional polymers which are first synthesized via copolymerization of either DL-lactide or L-lactide with epsilon-caprolactone. The polyol-terminated prepolymers are then converted to acrylic ester-terminated prepolymers, preferably by acylation of the alcohol terminus with acryloyl chloride via a Sohotten-Baumann-like technique, i.e., reaction of acyl halides with alcohols. The acrylic ester-terminated prepolymers may also be synthesized in other ways, such as reaction of carboxylic acids (i.e., acrylic or methacrylic acid) with alcohols, reaction of carboxylic acid esters (i.e., methyl acrylate or methyl methacrylate) with alcohols by transesterification, and reaction of isocyanatoalkyl acrylates (i.e. isocyanatoethyl methacrylate) with alcohols.

Adhesion formation after peritoneal surgery is a major cause of postoperative bowel obstruction, in fertility, and chronic pelvic pain. In addition, adhesion formation can occur after abdominal, gynecological, cardiac, thoracic, spinal, ENT, or orthopedic (e.g. tendon, joint, and knee) surgery. Therefore, a methodology by which adhesion formulation after surgery could be reduced or prevented would be of great benefit in reducing postoperative morbidity.

The most straightforward approach to reducing the incidence of adhesion formation remains physically maintaining the adhesiogenic surfaces apart with a mechanical barrier. For example, U.S. Pat. No. 6,403,655, assigned to Ethicon, Inc., describes a method of preventing adhesion formation between tissues by placing a polyoxaester adhesion prevention barrier between such tissues. Exemplified in the disclosure are a polyoxaester of 3,6-dioxaoctanedioic acid and ethylene glycol, as well as a copolymer of polyoxaester/caprolactone/glycolide.

U.S. Pat. No. 5,644,002 assigned to Ethicon, Inc., describes absorbable polymers and blends of polycondensation polyester and aliphatic polyesters based on lactone monomers, where the polycondensation polyester is the reaction product of diglycolic acid and an alcohol selected from the group consisting of glycerol, pentaerythitol, trimethylolpropane, hydroxyl terminated polyethylene glycols, ethylene glycol, 1,2-propanediol, 1,3-propanediol, 1,4-butylene glycol, dipropylene glycol, 1,5-pentanediol, 1,6-hexanediol, 1,7-heptanediol, and 1,8-octanediol. This reference teaches that the incorporation of hydroxyl terminated poly(ethylene glycol)s in the polycondensation polyester is desirable because it leads to polymers which are useful as adhesion prevention barriers. Additionally, this reference discloses that ultrathin coatings of about 1 to about 1000 microns can be applied to tissue surfaces for the prevention of adhesions. Some compositions of this reference may be used as soft tissue augmentation fillers.

U.S. Pat. Nos. 3,997,512, 4,048,256, 4,076,798, 4,095,600, 4,118,470, and 4,122,129 assigned to American Cyanamid Company, describe biocompatible and absorbable polycondensation polyesters, which are the polycondensation product of diglycolic acid and glycols such as ethylene glycol, diethylene glycol, 1,2-propylene glycol, 1,3-propylene glycol, and the like. Specifically, U.S. Pat. No. 4,095,600 describes a reaction product of (a) about 2 to 50% by weight of the polycondensation polyester and (b) polyglycolic acid, based on the total weight of the polycondensation polyester and polyglycolic acid, to form a self-supporting polymeric film for use, for example, in drug delivery. This reference is silent with respect to use of the composition for adhesion prevention.

SUMMARY OF THE INVENTION

In one aspect, the invention is directed to a co-polyester suitable for plastic and reconstructive surgery. The co-polyester includes the reaction product of a polycondensation polyester and epsilon-caprolactone, wherein the polycondensation polyester comprises the reaction product of diglycolic acid and/or a derivative thereof and a diol.

The co-polyester may comprise about 50 to about 80% by weight of the epsilon-caprolactone. The co-polyester may have Tg of about −30 to about −60° C. and weight average molecular weight of about 10,000 to about 30,000 g/mol.

Alternatively, the co-polyester may comprise about 60 to about 80% by weight of the epsilon-caprolactone, have Tg of about −50 to about −60° C. and weight average molecular weight of about 3,000 to about 10,000 g/mol.

An embodiment is directed to a process for preparing a co-polyester comprising reacting diglycolic acid and/or a derivative thereof with a diol to produce a dihydroxy poly (alkylene diglycolate) and/or a dihydroxy poly (diol diglycolate). Subsequently, a dihydroxy poly (alkylene diglycolate) and/or a dihydroxy poly (diol diglycolate) homopolymer is reacted with epsilon-caprolactone to produce the co-polyester which includes about 50 to about 80% by weight of the epsilon-caprolactone, based on the total weight of the co-polyester.

Another embodiment is directed to a process for preparing a co-polyester having weight average molecular weight of about 3,000 to about 10,000, comprising reacting diglycolic acid and/or a derivative thereof with ethylene glycol to produce poly(ethylene diglycolate) (PEDG), or with diethylene glycol to produce poly(ethoxyethylene diglycolate) (PEEDG), either one having weight average molecular weight of from about 1,000 to about 2,000 g/mol, and subsequently reacting the PEDG or PEEDG with an alcohol and epsilon-caprolactone to produce the co-polyester.

There is also provided a method of filling soft tissue comprising administering to the soft tissue a co-polyester which includes the reaction product of a polycondensation polyester and epsilon-caprolactone, wherein the polycondensation polyester comprises the reaction product of diglycolic acid and/or a derivative thereof and a diol. The co-polyester may have Tg of about −30 to about −60° C. and weight average molecular weight of about 10,000 to about 30,000 g/mol. Alternatively, the co-polyester may have Tg of about −50 to about −60° C. and weight average molecular weight of about 3,000 to about 10,000 g/mol.

In another aspect, the invention is directed to a method for preventing adhesion using a co-polyester of a different embodiment, which comprises the reaction product of a polycondensation polyester and at least one lactone, wherein the polycondensation polyester comprises the reaction product of diglycolic acid and/or a derivative thereof and ethylene glycol; and the co-polyester comprises about 40 to 50% by weight of the polycondensation polyester based on the total weight of the co-polyester.

BRIEF DESCRIPTION OF THE DRAWINGS

FIG. 1 presents a correlation between hydrolysis profiler and in vivo data for the absorbable polymers of Example 3.

DETAILED DESCRIPTION

1. Co-Polyesters and Use Thereof for Plastic and Reconstructive Surgery

In this application a discussion of a singular component, composition or ingredient includes the discussion of plurality thereof and vice versa. For example, discussion (or disclosure) of a co-polyester also includes disclosure of co-polyesters.

Unless indicated otherwise, inherent viscosity (IV) measurements included in the application are obtained by conducting the measurements in a 0.1 g/dL solution of hexafluoroisopropanol (HFIP) at 25° C.

The co-polyester of this embodiment and composition(s) including such co-polyester are relatively long lasting absorbable synthetic fillers that minimize or eliminate frequent body injections. The co-polyester and composition(s) are liquid at ambient conditions and/or at the temperature of a human body. In addition, the co-polyester of this embodiment comprises a hydrophilic poly(ethylene diglycolate) component (or similar hydrophilic components) that, when injected into aqueous media, allows partial swelling of the co-polyester implant making the material very soft, fully compressible but yet such that it maintains its shape during long residual time. The polymers (i.e., co-polyesters) of this embodiment are liquids or soft solids with the inherent viscosities (IV) ranging between about 0.25 to about 0.90 dL/g. This viscosity range is high enough to minimize tissue reactions that are often associated with low molecular weight polymers. A composition comprising the co-polyester and a certain amount of a biocompatible solvent, such as benzyl benzoate or tetraglycol, allows for less painful polymer injections with minimal tissue reactions. In an alternative type of a co-polyester included in this embodiment (discussed below), the co-polyester has inherent viscosities (IV) ranging between about 0.10 to about 0.30 dL/g.

The co-polyester of this embodiment (and a composition containing it) has properties which make it suitable for plastic and reconstructive surgery applications. Thus, the co-polyester and the composition are injectable, absorbable liquid polymer formulations (at ambient conditions and/or at human body temperature). The co-polyesters are long-absorbable fillers, i.e., they hydrolyze substantially completely in vivo, in an animal, such as a human, not later than about 700 days, such as not later than about 560 days, e.g., within about 15 to about 18 months, or within about 300 to about 700 days from the time of administration of the co-polyesters into the tissue.

Two types of co-polyesters are included in this embodiment: A) high molecular weight (MW) co-polyesters; and B) low MW co-polyesters.

A. High MW Co-Polyesters

The high MW co-polyesters have Tg (glass transition temperature) of about −30 to about −60° C., such as about −35 to about −55° C., or about −38.5 to about −55° C., and they include about 50 to about 80%, such as about 50 to about 70% by weight, of the epsilon-caprolactone component, based on the total weight of the co-polyester. The co-polyester has melt viscosity of about 10,000 to about 120,000, such as about 11,000 to about 100,000, or about 11,500 to about 60,000 cps (centipoise). The co-polyester comprises from about 20 to about 50% by weight of the polycondensation polyester based on the total weight of the co-polyester. The polycondensation polyester has Tg of about 5 to about −20° C., such as about 0 to about −15° C.

The co-polyester includes the reaction product of a polycondensation polyester and epsilon-caprolactone, added in the second, ring-opening polymerization ("ROP") stage. The polycondensation polyester comprises the reaction product of diglycolic acid and/or a derivative thereof and a diol. The derivative of the diglycolic acid may be 3,6-dioxaoctanedioic acid, 3,6,9-trioxaundecanedioic acid, and combinations thereof. Suitable diols include, without limitations, ethylene glycol, diethylene glycol (DEG), and N-methyldiethanolamine (NMDEA).

The co-polyester of this embodiment is prepared as discussed below.

The polycondensation polyester may be synthesized by conventional techniques using conventional processes. For example, in a condensation polymerization, diglycolic acid and ethylene glycol may be polymerized in the presence of a catalyst at elevated temperatures and reduced pressures. A variety of catalysts may be used, but organometallic compounds have been found to be useful.

The catalyst for the polycondensation step of the synthesis is preferably tin based, e.g., stannous octoate. The most desirable catalyst is dibutyltin oxide which is present in the diglycolic acid/ethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 180° C., under an inert atmosphere until esterification of diglycolic acid is complete. Preferably, 165° C. has been found to be a desirable reaction temperature when employing a vertically stirred reactor. It should be noted that the optimum reaction temperature may be reactor and catalyst level dependent but can be found by one having ordinary skill in the art through routine experiments. The first stage of the polycondensation reaction (inert gas at atmospheric pressure) is followed by polymerization under reduced pressure until the desired molecular weight and viscosity are achieved. Instead of ethylene glycol, other diols may be used, such as, diethylene glycol (DEG), or N-methyldiethanolamine (NMDEA). When other diols are used, synthesis of the polycondensation polyester may be conducted in a similar manner, as will be apparent to skilled persons.

The weight average molecular weight of the polycondensation polymer (i.e., polycondensation polyester) can range from about 5,000 to about 30,000 g/mol, from about 7,000 to about 20,000 g/mol, or can be about 10,000 g/mol. This corresponds to an inherent viscosity (IV) range from about 0.25 to about 0.60 dL/g.

The amount of polycondensation polyester used to prepare the co-polyester is about 20 to about 50% by weight, based on the total weight of the co-polyester.

The co-polyester of this embodiment may be conveniently synthesized by the reaction of a dihydroxy poly (alkylene diglycolate) or a dihydroxy poly (diol diglycolate) homopolymer with the epsilon-caprolactone by conventional techniques using conventional processes. For example, the polycondensation polyester, made with a diol, is used as an α,ω-dihydroxy macroinitiator in a subsequent ring opening polymerization (ROP) with the epsilon-caprolactone. The epsilon-caprolactone monomer is copolymerized into the polycondensation polyester in the presence of a conventional organometallic catalyst at elevated temperatures. The catalyst for the ROP may be already present as residual catalyst in the polycondensation polyester or an additional catalyst may be added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of the epsilon-caprolactone monomer-to-catalyst ranging from about 20,000/1 to infinity (i.e., no additional catalyst used). Thus one might utilize a tin-IV compound such as dibutyltin oxide as a diacid, for instance, diglycolic acid-to-catalyst ratio of about 10,000/1 to prepare the polycondensation polyester and then add a tin-II compound such as stannous octoate at an epsilon-caprolactone-to-added-catalyst molar ratio of about 240,000/1 at the time of the ring opening polymerization. The co-polyesters of the present invention may be synthesized alternately with no additional catalyst being added at the time of the ROP as described in Example 10A. While this example describes the co-polyesters of a different embodiment, persons of ordinary skill will readily understand how to adapt principles thereof to this embodiment of the invention.

The ROP step can be immediately conducted in the same reactor as that used to synthesize the polycondensation polyester immediately after the completion of the polycondensation step, if the reactor can provide adequate heat transfer and agitation. The epsilon-caprolactone can be added as a liquid. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. The epsilon-caprolactone is then added. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the co-polyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 190° C. in one embodiment, and held there for typically 18-20 hours. The exact reaction conditions will depend on the catalyst and its level; final reaction temperatures can vary from about 180° C. to about 210° C. and more preferably from about 190° C. to about 200° C. Reaction times can vary from about 2 hours to about 20 hours, depending on the catalyst and its level, and typically the reaction is conducted until the desired conversion of monomer to polymer is achieved.

Under the above described conditions, the co-polyesters of polycondensation polyester and epsilon-caprolactone will typically have a weight average molecular weight (MW) of about 10,000 to about 30,000, such as about 12,000 to about 26,000, or about 15,000 to about 25,000 g/mol (a.k.a. Daltons). These molecular weights correspond to inherent viscosity, typically between about 0.25 to about 0.90 deciliters per gram (dL/g), such as about 0.50 to about 0.80 dL/g, about 0.60 to about 0.70 dL/g, or about 0.65 dL/g, as measured in a 0.1 g/dL solution of hexafluoroisopropanol (HFIP) at 25° C.

The co-polyester may be used in the plastic or reconstructive surgery as is, or in a composition (also referred to herein as a "formulation"), which includes the co-polyester and a biocompatible solvent. Suitable biocompatible solvents include, without limitations benzyl benzoate, tetraglycol, triacetin, Tween 20 (Polysorbate 20), Poly(ethylene glycol) sorbitan ether monolaurate and Tween80 (Polysorbate 80), Poly (ethylene glycol) sorbitan ether monooleate. The amount of the solvent in the formulation is such that it decreases pain associated with polymer injections. For example, the formulation may contain about 5% to about 60%, such as about 10% to about 50%, about 20% to about 40% by volume of the biocompatible solvent. The formulation may have melt viscosity of about 50 to about 20,000, such as about 100 to about 10,000, or about 1,000 to about 5,000 cps.

B. Low MW Co-Polyesters

As discussed above, in another aspect of this embodiment, the co-polyester has lower weight average molecular weight, and lower IV. These low viscosity, low MW materials allow injections through small needle size without using an organic solvent, or if the solvent is necessary, using it in relatively small concentrations. The weight average molecular weight of such co-polyester is about 3,000 to about 10,000, such as about 4,000 to about 6,000, or about 5,000 g/mol, and its IV is about 0.10 to about 0.35, such as about 0.2 to about 0.3, or about 0.25 dL/g. $T_g$ of this co-polyester is about −50° C. to about −60° C., such as about −55° C. This co-polyester includes about 60 to about 80% by weight of the epsilon-caprolactone, and about 20 to about 40% by weight of the polycondensation polyester, based on the total weight of the co-polyester. This co-polyester has melt viscosity of about 5,000 to about 50,000, such as about 10,000 to about 40,000, or about 20,000 to about 25,000 cps (centipoise).

Such co-polyester is prepared by a slightly modified process. In particular, syntheses of such co-polyesters are accomplished by initially synthesizing a low molecular weight PEDG by reacting diglycolic acid with ethylene glycol, or low molecular weight PEEDG by reacting diglycolic acid with diethylene glycol. Then, to the PEDG or PEEDG (each of which may be referred to as a poly condensation polymer) is added an extra alcohol, such as diols (e.g., DEG, NMDEA) or a multi-hydroxyl alcohol (Quadrol, N,N,N',N'-tetra(2-hydroxypropyl)ethylene diamine), in the second copolymerization step conducted with epsilon-caprolactone, as illustrated in Examples 3A, 3B, 7A-7E. The weight average molecular weight of the PEDG or PEEDG can range from about 1,000 to about 2,000 g/mol. The PEDG or PEEDG (i.e., polycondensation polyester) has Tg of about −50 to about −60° C., such as about −55° C. Otherwise, synthesis of such low MW co-polyesters is carried out in substantially the same manner as that of the high MW co-polyesters, described above.

For all types and embodiments of co-polyesters used for plastic and reconstructive surgery, when the molecular weight of the polycondensation polymer is lower than about 1,000 g/mol, the molecular weight of the final co-polyester is too low to achieve the desired properties necessary for the plastic and reconstructive surgery applications of the co-polyester. Although molecular weight can be increased with increasing reaction time, it becomes increasingly difficult to achieve very high molecular weight. We have found, in general, that a molecular weight of the polycondensation polymer greater than about 30,000 g/mol, is not necessary to achieve desirable properties. One could however envision that this value is not an absolute bar. One might for instance, increase the molecular weight of the polycondensation polymer, and lower the amount of the epsilone-copralactone component used in the preparation of the final co-polyester.

Prior to the use of any of the co-polyesters of this embodiment for filling soft tissue (discussed below), the co-polyesters can be sterilized by conventional techniques, e.g., by gamma (γ)-irradiation (20 Kgy). An interesting and important property of the co-polyesters is the substantial absence therein of residual monomers, before or after sterilization. As will be appreciated by those skilled in the art, this is a very desirable property, since some heretofore known polymers used for similar applications have been known to cause adverse tissue reactions attributed to the presence of monomers in the polymers.

A further aspect of the invention relates to a method of filling soft tissue, e.g., in a human, comprising administering any of the co-polyesters of this embodiment, either by themselves or in the composition which includes the co-polyester(s) and a biocompatible solvent. The method may be used for plastic or reconstructive surgery applications of soft tissue, such as the face of a patient, e.g., for lip augmentation, lip reconstruction or body contouring.

The method typically comprises administering the co-polyester, or the composition including the co-polyester, by injecting the co-polyester or the composition, into the subcutaneous layer of the skin in the embodiments wherein the facial cosmetic or reconstructive surgery is desired. In the embodiment wherein the co-polyester or composition is intended for lip augmentation or lip reconstruction, the injecting is above the muscle tissue of the lip. Depending on the afflicted area, the amount of the co-polyester or the composition used may vary, as will be apparent to those skilled in the art.

The method may comprise one or more than one injection to cover the desired area or to achieve the desired result.

All examples in this application are presented for illustrative purposes only, and they do not limit the scope of the disclosure, which is defined by the entire specification and claims.

EXAMPLE 1

Synthesis of Hydroxy Terminated Polyethylene Diglycolate) (PEDG)

A twin-agitated reactor with intermeshing HELICONE patterned blades (Atlantic 10CV reactor) was employed. After charging the reactor with 10.0 kg of diglycolic acid, 13.9 kg of ethylene glycol (EG) and 1.86 grams of dibutyltin oxide catalyst, the pressure was reduced to below 1 Torr and the vacuum preserved over night. The next day vacuum was released with dry nitrogen (argon can be substituted) and the heating of mixture started. When the reactor temperature reached 150° C., an agitator speed was set to 30 RPM. Soon first distillate appeared containing mostly water, an esterification by-product. The reaction was continued at 165° C. for a couple of more hours until approximately all water was distilled and/or first traces of EG appeared in the distillate. After the first nitrogen/argon stage was completed, pressure was lowered gradually to full vacuum in steps while the temperature of the batch was maintained at 165° C. A vacuum of about 30-50 mTorr was maintained throughout the rest of the reaction. Melt and solution viscosities were regularly checked to ensure a polymer of a desired molecular weight. A hydroxy end-capped polymer was discharged after 75 hours of reaction time under vacuum. It was a fully amorphous, colorless viscous liquid with a glass transition temperature of about 3° C. Weight average molecular weight was 12,000 g/mol; the resin exhibited an inherent viscosity (IV) of 0.35 dL/g as determined in HFIP at 25° C. at a concentration of 0.1 g/dL.

EXAMPLE 2

Example 2 includes general description of the copolymerization step; specific examples of the individual samples follow in Examples 2A, 2B and 2C.

Co-Polymerization of Hydroxy Terminated Poly(Ethylene Diglycolate) with a Lactone Monomer, Epsilon-Caprolactone A portion of the Polyethylene diglycolate made in Example 1 was added into an oven dried 250 milliliter round bottom flask. In the nitrogen glove box, the e-caprolactone and catalyst were charged. A mechanical stirrer, nitrogen adapter and stirrer bearing were added to the 250 ml flask's neck opening. The vessel was pulled under a vacuum of less than 500 mTorr at room temperature and held overnight. The polymer was reacted using a stepped temperature profile. The next day the flask was released to nitrogen and placed in the oil bath. The bath temperature was set to 120° C. without agitation. Once the temperature reached approximately 95° C. the mechanical stirrer was set at 4 RPM. When the temperature reached 120° C., the oil bath setpoint was increased to 160° C. and the mixing was increased to 6 RPM. When the melt appeared homogenous and clear, the agitation was reduced to ½ RPM and the temperature was raised to 190° C. for 19 hours±1 hour. After 19 hours±1 hour the reaction was stopped and allowed to cool overnight under nitrogen.

All the glass inserts were removed from the flask, leaving only the mechanical stirrer, polymer resin and the round bottom flask. The flask was then wrapped in aluminum foil and the polymer product was removed from the reaction flask through liquid nitrogen quenching. The remaining glass shards were ground/sanded off of the polymer product. The polymer fragments were collected and placed in a Teflon coated pan. The pan was placed in the vacuum oven and pulled under vacuum overnight. The next day the vacuum oven was set to 110° C. and the polymer was devolitized for 16 hours.

EXAMPLE 2A

The Copolymerization of Hydroxy Terminated Poly(Ethylene Diglycolate) with a Epsilon-Caprolactone; PEDG/Cap 50/50 wt. %

A portion of the Poly(ethylene diglycolate) made in Example 1 (50 g) that was discharged after 28 hours (IV=0.25 dL/g) was placed into an oven dried 250 milliliter round bottom flask. In the nitrogen glove box, the e-caprolactone (50 g) and catalyst, stannous octoate (0.022 mL) were charged. A mechanical stirrer, nitrogen adapter and stirrer bearing were added to the 250 ml flask's neck opening. The vessel was pulled under a vacuum of less than 200 mTorr at room temperature and held overnight. The next day the flask was released to nitrogen and placed in the oil bath. The bath temperature was set to 120° C. without agitation. Once the temperature reached approximately 95° C. the mechanical stirrer was set at 4 RPM. When the temperature reached 120° C., the oil bath setpoint was increased to 160° C. and the mixing was increased to 6 RPM. When the melt appeared homogenous and clear, the agitation was reduced to 0.5 RPM and the temperature was raised to 190° C. for 18 hours. After 18 hours the reaction was stopped and allowed to cool overnight under nitrogen.

All the glass inserts were removed from the flask, leaving only the mechanical stirrer, polymer resin and the round bottom flask. The flask was then wrapped in aluminum foil and the polymer product was removed from the reaction flask through liquid nitrogen quenching. The remaining glass shards were ground/sanded off of the polymer product. The polymer fragments were collected and placed in a Teflon coated pan. The pan was placed in the vacuum oven and pulled under vacuum overnight. The next day the vacuum oven was set to 110° C. and the polymer was devolitized for 16 hours to remove any residual monomer. The discharged material was slightly yellowish, free flowing material at ambient condition with the weight average molecular weight of 15,000 g/mol, and the inherent viscosity of 0.48 dL/g.

EXAMPLE 2B

The Copolymerization of Hydroxy Terminated Poly(Ethylene Diglycolate) with a Epsilon-Caprolactone; PEDG/Cap 40/60 wt. %

A portion of the poly(ethylene diglycolate) made in Example 1 (40 g) was added into an oven dried 250 milliliter round bottom flask. In the nitrogen glove box, the e-caprolactone (60 g) and catalyst, stannous octoate (0.027 mL) were charged. A mechanical stirrer, nitrogen adapter and stirrer bearing were added to the 250 ml flask's neck opening. The vessel was pulled under a vacuum of less than 200 mTorr at room temperature and held overnight. The next day the flask was released to nitrogen and placed in the oil bath. The bath temperature was set to 120° C. without agitation. Once the temperature reached approximately 95° C. the mechanical stirrer was set at 4 RPM. When the temperature reached 120° C., the oil bath setpoint was increased to 160° C. and the mixing was increased to 6 RPM. When the melt appeared homogenous and clear, the agitation was reduced to 0.5 RPM and the temperature was raised to 190° C. for 19 hours. After 19 hours the reaction was stopped and allowed to cool overnight under nitrogen.

All the glass inserts were removed from the flask, leaving only the mechanical stirrer, polymer resin and the round bottom flask. The flask was then wrapped in aluminum foil and the polymer product was removed from the reaction flask through liquid nitrogen quenching. The remaining glass shards were ground/sanded off of the polymer product. The polymer fragments were collected and placed in a Teflon coated pan. The pan was placed in the vacuum oven and pulled under vacuum overnight. The next day the vacuum oven was set to 110° C. and the polymer was devolitized for 16 hours to remove any residual monomer. The discharged material was slightly yellowish, free flowing material at ambient condition with the weight average molecular weight of 22,000 g/mol, and the inherent viscosity of 0.70 dL/g.

EXAMPLE 2C

The Copolymerization of Hydroxy Terminated Poly(Ethylene Diglycolate) with a Epsilon-Caprolactone; PEDG/Cap 30/70 wt. %

A portion of the Poly(ethylene diglycolate) made in Example 1 (30 g) was added into an oven dried 250 milliliter round bottom flask. In the nitrogen glove box, the e-caprolactone (70 g) and catalyst, stannous octoate (0.031 mL) were charged. A mechanical stirrer, nitrogen adapter and stirrer bearing were added to the 250 ml flask's neck opening. The vessel was pulled under a vacuum of less than 300 mTorr at room temperature and held overnight. The next day the flask was released to nitrogen and placed in the oil bath. The bath temperature was set to 120° C. without agitation. Once the temperature reached approximately 95° C. the mechanical stirrer was set at 4 RPM. When the temperature reached 120° C., the oil bath setpoint was increased to 160° C. and the mixing was increased to 6 RPM. When the melt appeared homogenous and clear, the agitation was reduced to 0.5 RPM and the temperature was raised to 190° C. for 20 hours. After 20 hours the reaction was stopped and allowed to cool overnight under nitrogen.

All the glass inserts were removed from the flask, leaving only the mechanical stirrer, polymer resin and the round bottom flask. The flask was then wrapped in aluminum foil and the polymer product was removed from the reaction flask through liquid nitrogen quenching. The remaining glass shards were ground/sanded off of the polymer product. The polymer fragments were collected and placed in a Teflon coated pan. The pan was placed in the vacuum oven and pulled under vacuum overnight. The next day the vacuum oven was set to 110° C. and the polymer was devolitized for 16 hours to remove any residual monomer. The discharged material was slightly yellowish, waxy material at ambient condition with the weight average molecular weight of 24,000 g/mol, and the inherent viscosity of 0.72 dL/g.

EXAMPLES 3A and 3B

In Examples 3A and 3B, the same types of copolymers were prepared as in the above Examples, except that in the polycondensation step (similar to Example 1) a different diol was used: diethylene glycol (DEG), instead of ethylene glycol in Example 3B.

We found that physical properties of the copolymers containing DEG instead of ethylene glycol in the structure were not altered significantly. With the DEG-containing material we observed a slight increase in viscosity.

EXAMPLE 3A

Synthesis of Hydroxy Terminated Poly(Ethoxyethylene Diglycolate) (PEEDG)

A dual-agitated reactor with intermeshing HELICONE patterned blades (D.I.T. 10CV reactor) was employed. After charging the reactor with 7.0 kg of diglycolic acid, 16.6 kg of diethylene glycol (DEG) and 1.3 grams of dibutyltin oxide catalyst, the pressure was reduced to below 1 Torr and the vacuum preserved over night. The next day vacuum was released by introducing dry nitrogen (argon can be substituted) and heating of the mixture was started, and the agitator was stared and set to 15 RPM in reverse. When the reactor temperature reached 150° C., the agitator speed was reset to 20 RPM in forward direction. Soon first distillate appeared containing mostly water, an esterification by-product. The reaction was continued at 170° C. for about 2 hours until approximately all water was distilled and/or first traces of EG appeared in the distillate. After the first nitrogen/argon stage was completed, pressure was lowered gradually to full vacuum while the temperature of the batch was maintained at 170° C. A vacuum of about 30-50 mTorr was maintained throughout the rest of the reaction, a total time of approximately 80 hours. Melt and solution viscosities were regularly checked to ensure polycondensation polyester of a desired molecular weight. Hydroxy end-capped polycondensation polyester was discharged after different reaction time under vacuum. The discharged sample was a fully amorphous, colorless viscous liquid with a glass transition temperature of about −15.0° C.

EXAMPLE 3B

Synthesis of Lower Molecular Weight Copolyesters for Solventless Injections: PEEDG/Cap 30/70 with Diethylene Glycol, DEG A portion of the lower molecular weight poly(ethoxyethylene diglycolate) (30 g) made as in Example 3A (IV=0.14 dL/g) was added into an oven dried 250 milliliter round bottom flask. In the nitrogen glove box, the e-caprolactone (70 g), an additional amount of DEG (2.50 mL) and catalyst, stannous octoate (0.030 mL) were charged. A mechanical stirrer, nitrogen adapter and stirrer bearing were added to the 250 ml flask's neck opening. The vessel was pulled under a vacuum of less than 300 mTorr at room temperature and held overnight. The next day the flask was released to nitrogen and placed in the oil bath. The bath temperature was set to 120° C. without agitation. Once the temperature reached approximately 95° C. the mechanical stirrer was set at 1 RPM. When the temperature reached 120° C., the oil bath setpoint was increased to 160° C. and the mixing was increased to 2 RPM. When the melt appeared homogenous and clear, the agitation was reduced to 1 RPM and the temperature was raised to 190° C. for 19 hours. After 19 hours the reaction was stopped and allowed to cool overnight under nitrogen.

All the glass inserts were removed from the flask, leaving only the mechanical stirrer, polymer resin and the round bottom flask. The polymer product was removed from the still hot reaction flask by pouring it directly into weighted Teflon coated pan. The pan was placed in the vacuum oven and kept under vacuum overnight. The next day the vacuum oven was set to 110° C. and the polymer was devolitized for 16 hours to remove any residual monomers. The final co-polyester is colorless, free flowing material at ambient conditions with the weight average molecular weight of 8,800 g/mol, and the melt viscosity of 50,000 cps as measured at 23° C.

EXAMPLE 3C

Selected Physical Characteristics of Injectable Copolyesters

Copolyesters based on different weight ratios of poly(ethylene diglycolate) and epsilon-caprolactone were prepared according to Examples 2A-2C. Physical properties of these injectable formulations were tested and data summarized in Table 1. In-vitro absorption profile data were obtained using the automatic titration unit set at 75° C. using NaOH as a Base. Prediction data for the in-vivo response (last column) were obtained using a correlation diagram between hydrolysis profiler data (time to achieve 90% degradation at 75° C.) and in-vivo absorption time available for corresponding known materials. The correlation between hydrolysis profiler and in vivo data is presented in FIG. 1.

TABLE 1

| EX. | Polymer Composition | Mw (g/mol)/ IV (dL/g) | Tg (° C.) | Cryst. [ΔH (J/mol)] | Tm (° C.) | In-vitro absorption rate [$t_{90\%}$@ 75° C. in days] | Correlated* In-vivo absorption rate [days] |
|---|---|---|---|---|---|---|---|
| 2A | PEDG/Cap 50/50 wt. % | 15,000/0.48 | −38.5 | 0 | — | 8 | 430 |
| 2B | PEDG/Cap 40/60 wt. % | 22,000/0.70 | −45.5 | 0 | — | 10 | 538 |

TABLE 1-continued

| EX. | Polymer Composition | Mw (g/mol)/ IV (dL/g) | Tg (°C.) | Cryst. [ΔH (J/mol)] | Tm (°C.) | In-vitro absorption rate [t$_{90\%}$@ 75° C. in days] | Correlated* In-vivo absorption rate [days] |
|---|---|---|---|---|---|---|---|
| 2C | PEDG/Cap 30/70 wt. % | 24,000/0.72 | −46.5 | 22 | 38.5 | 13 | 695 |

*based on in-vivo vs. in-vitro correlation curve given below.

The results from the last column indicate that all copolymers 2A, 2B and 2C may fulfill the requirements for long absorbable fillers—to hydrolyze completely in around 18 months (540 days). Fine-tuning the composition to reach desired absorption time may also be possible.

The absorbable polymers used to make the correlation of FIG. 1 were: Vicryl (coated, undyed), Monocryl, PDS2, 0% LAC/100% GLY, 4% LAC/96% GLY, 8% LAC/92% GLY, 12% LAC/88% GLY, 18% LAC/82% GLY and Vicryl #2 film.

EXAMPLES 4A and 4B

Solvent Study—Benzyl Benzoate, BB (Example 4A) and Tetraglycol (Example 4B)

A small portion (5 g) of each polymer (Examples 2A, 2B and 2C) was placed in a 50-milliliter jar. The jar was filled approximately ¼ of the way with 5 g of Benzyl Benzoate, BB or Tetraglycol. Benzyl Benzoate is a more hydrophobic solvent, Tetraglycol is known to exchange relatively quickly in a body with water. The jars were then placed on the Multi-Wrist Shaker. The shaker was set on a speed of 8 for a continuous cycle. The jars were monitored and the observations were recorded. These data are summarized below in Tables 2A and 2B.

TABLE 2A (for BB).

| Polymer Example # | Concentration Polymer/BB [wt. %] | Time to Dissolve @ Room Temperature | Comments |
|---|---|---|---|
| 2A | 50/50 | 22 hours | Complete dissolution |
| 2B | 50/50 | 17 hours | Complete dissolution |
| 2C | 33/67 | 48 hours | 50/50 concentration would not dissolve @ room temperature nor when heated to 75° C. for 9 hours |

TABLE 2B (for Tetraglycol).

| Polymer Example # | Concentration Polymer/ Tetraglycol [wt. %] | Time to Dissolve @ Room Temperature | Comments |
|---|---|---|---|
| 2A | 50/50 | ≤14 hours (completed overnight) | Complete dissolution |
| 2B | 50/50 | ≤14 hours | Complete dissolution |
| 2C | 50/50 | ≤14 hours | Complete dissolution when heated initially to 75° C. for a couple of minutes |

All three co-polymers of Examples 2A, 2B and 2C are soluble completely in these solvents at 50/50 wt. % ratio, except the co-polymer of Example 2C in BB, where higher concentration of the solvent is needed to complete dissolution. The time to dissolve the co-polymers in these solvents can be dramatically reduced by the application of heat. Also, the use of heating may allow dissolution of a higher polymer concentration if necessary.

TABLE 3

The effect of γ-irradiation (20 Kgy) on the physical properties of polymers

| | | | NMR composition in wt. % | | | |
|---|---|---|---|---|---|---|
| Example | Melt Viscosity (cps) | IV (g/dL)/M$_w$ (g/mol) | PEDG-2 | PCL | ε- cap, monomer residue | BB |
| PEDG/Cap 50/50 (Example 2A), Non-sterile | 27,200 (@80° C.) | 0.48/15,000 | NA | NA | NA | / |
| PEDG/Cap 50/50 (Example 2A), Sterile | 27,600 (@80° C.) | 0.48/13,000 | 49.5 | 50.5 | 0.0 | / |

TABLE 3-continued

The effect of γ-irradiation (20 Kgy) on the physical properties of polymers

|  | Melt Viscosity (cps) | IV (g/dL)/$M_w$ (g/mol) | NMR composition in wt. % | | | |
|---|---|---|---|---|---|---|
| Example |  |  | PEDG-2 | PCL | ε-cap, monomer residue | BB |
| PEDG/Cap 40/60 (Example 2B), Non-sterile | 120,000 (@80° C.) | 0.70/22,000 | NA | NA | NA | / |
| PEDG/Cap 40/60 (Example 2B), Sterile | 115,000 (@80° C.) | 0.67/20,000 | 39.8 | 60.2 | 0.0 | / |
| PEDG/Cap 50/50 (Example 2A), with BB Non-sterile | 6,000 (@30° C.) | N/A/15,000 | 23.0 | 23.3 | 0.0 | 53.7 |
| PEDG/Cap 50/50 (Example 2A), with BB Sterile | 7,300 (@30° C.) | N/A/14,000 | 24.0 | 24.4 | 0.0 | 51.6 |
| PEDG/Cap 40/60 (Example 2B), with BB non-Sterile | 15,300 (@30° C.) | NA/20,000 | 17.8 | 27.0 | 0.0 | 55.2 |
| PEDG/Cap 40/60 (Example 2B), with BB Sterile | 21,800 (@30° C.) | NA/20,000 | 18.8 | 28.4 | 0.0 | 52.8 |
| PEDG/Cap 30/70 (Example 2C), with BB non-Sterile | 14,600 (@30° C.) | NA/22,000 | 13.0 | 28.3 | 0.0 | 58.7 |
| PEDG/Cap 30/70 (Example 2C), with BB Sterile | 19,900 (@30° C.) | NA/24,000 | 14.7 | 30.9 | 0.0 | 54.4 |

These data indicate several important characteristics:
a.) An addition of a solvent reduces greatly the viscosity of the system, which enables the easier injections through smaller needle.
b.) There is only a very small loss in molecular weight for polymers as neat resin formulations after the irradiation; furthermore, we observed no change in the molecular weight or inherent viscosity of polymers that are dissolved in benzyl benzoate after the irradiation step.
c.) There is no residual monomer present in any formulations before or after sterilization, which is desirable to minimize possible tissue reaction that may arise from the presence of the monomers.

EXAMPLE 6

Viscosity and Injection Force Study
Viscosity Test Conditions:
Rheometer: Bohlin CVOR-120.
Viscometry Mold: Strain Rate Ramp (step): 0.04 to 10 1/s.
Settings: Delay time 40 seconds, Integration time 40 seconds.
Geometry: 20 mm Parallel Plate with the gap of 1 mm.
Test Temperature: 24° C.
Sample History: 1 week storage at room temperature
    n=2 tests per formulation, no pre-shear before testing.
Test Parameters for Injection Force Measurements:
Syringe: 500 μL
Needle: 21 gauge—1 inch
Injection Speed: 1 ml/minute
Room Temperature Testing
Sample History: Refrigerator overnight; 2 hour equilibrium at RT (room temperature) before the test

TABLE 4

Injection force and viscosity data for polymers as a function of solvent Concentration

| POLYMER | Benzyl Benzoate (% wt.) | Injection Force (N) | Melt Viscosity (poise) |
|---|---|---|---|
| PEDG/Cap 50/50 | 20 | >300 | 5,000 |
| PEDG/Cap 50/50 | 40 | 88 | 600 |
| PEDG/Cap 50/50 | 60 | 11 | 60 |
| PEDG/Cap 40/60 | 20 | >300 | 8,000 |
| PEDG/Cap 40/60 | 40 | 111 | 1,000 |
| PEDG/Cap 40/60 | 60 | 30 | 110 |
| PEDG/Cap 30/70 | 20 | >300 | 20,000 |
| PEDG/Cap 30/70 | 40 | 143 | 1,000 |
| PEDG/Cap 30/70 | 60 | 30 | 120 |

Note:
In all solvent present formulations, except PEDG/Cap 30/70 with 20% BB that shows certain shear-thinning effect, a perfect Newtonian behavior was observed - no change in viscosity can be detected as a function of shear rate. An injection force of about 50-60N is considered effortless for the syringe injections.

EXAMPLE 7

Lower Molecular Weight Copolyesters for Solventless Injections

A series of lower molecular weight copolyesters of PEDG/Cap have been made that posses lower viscosity than polymer samples of Examples 2A, 2B and 2C. These low viscosity materials allow injections through small needle size without using an organic solvent, or if it is necessary, using it in relatively small concentrations. Syntheses of these materials are accomplished by utilizing an initially small molecular weight of polyethylene diglycolate (PEDG), and adding the extra diol (DEG) in the second, copolymerization step. Individual examples of each of these polymers are discussed in Examples 7A-7E. In Examples 7A-7E, synthesis of the lower molecular weight copolyesters includes the use of a portion of the lower molecular weight poly(ethylene diglycolate) made in Example 1, having IV of .11 dL/g. This portion was obtained by removing it from the reactor prior to the final discharge.

EXAMPLE 7A

Synthesis of Lower Molecular Weight Copolyesters for Solventless Injections: PEDG/Cap 40/60 with Diethylene Glycol, DEG A portion of the lower molecular weight Poly(ethylene diglycolate) (40 g) made as in Example 1 (IV=0.11 dL/g) was added into an oven dried 250 milliliter round bottom flask. In the nitrogen glove box, the e-caprolactone (60 g), an additional amount of DEG (2.47 mL) and catalyst, stannous octoate (0.027 mL) were charged. A mechanical stirrer, nitrogen adapter and stirrer bearing were added to the 250 ml flask's neck opening. The vessel was pulled under a vacuum of less than 300 mTorr at room temperature and held overnight. The next day the flask was released to nitrogen and placed in the oil bath. The bath temperature was set to 120° C. without agitation. Once the temperature reached approximately 95° C. the mechanical stirrer was set at 1 RPM. When the temperature reached 120° C., the oil bath setpoint was increased to 160° C. and the mixing was increased to 2 RPM. When the melt appeared homogenous and clear, the agitation was reduced to 0.75 RPM and the temperature was raised to 190° C. for 17 hours. After 17 hours the reaction was stopped and allowed to cool overnight under nitrogen.

All the glass inserts were removed from the flask, leaving only the mechanical stirrer, polymer resin and the round bottom flask. The polymer product was removed from the still hot reaction flask by pouring it directly into weighted Teflon coated pan. The pan was placed in the vacuum oven and kept under vacuum overnight. The next day the vacuum oven was set to 110° C. and the polymer was devolitized for 16 hours to remove any residual monomers. The final copolyester is colorless, free flowing material at ambient conditions with the weight average molecular weight of 4,400 g/mol, inherent viscosity of 0.22 dL/g, and the melt viscosity of 31,000 cps as measured at 23° C.

EXAMPLE 7B

Synthesis of Lower Molecular Weight Copolyesters for Solventless Injections: PEDG/Cap 30/70 with Diethylene Glycol, DEG A portion of the lower molecular weight Poly(ethylene diglycolate) (30.7 g) made as in Example 1 (IV=0.11 dL/g) was added into an oven dried 250 milliliter round bottom flask. In the nitrogen glove box, the e-caprolactone (72.8 g), an additional amount of DEG (2.50 mL) and catalyst, stannous octoate (0.032 mL) were charged. A mechanical stirrer, nitrogen adapter and stirrer bearing were added to the 250 ml flask's neck opening. The vessel was pulled under a vacuum of less than 300 mTorr at room temperature and held overnight. The next day the flask was released to nitrogen and placed in the oil bath. The bath temperature was set to 120° C. without agitation. Once the temperature reached approximately 95° C. the mechanical stirrer was set at 1 RPM. When the temperature reached 120° C., the oil bath setpoint was increased to 160° C. and the mixing was increased to 2 RPM. When the melt appeared homogenous and clear, the agitation was reduced to 0.75 RPM and the temperature was raised to 190° C. for 18.5 hours. After 18.5 hours the reaction was stopped and allowed to cool overnight under nitrogen.

All the glass inserts were removed from the flask, leaving only the mechanical stirrer, polymer resin and the round bottom flask. The polymer product was removed from the still hot reaction flask by pouring it directly into weighted Teflon coated pan. The pan was placed in the vacuum oven and kept under vacuum overnight. The next day the vacuum oven was set to 110° C. and the polymer was devolitized for 16 hours to remove any residual monomers. The final copolyester is colorless, free flowing material at ambient conditions with the weight average molecular weight of 4,800 g/mol, inherent viscosity of 0.24 dL/g, and the melt viscosity of 20,000 cps as measured at 23° C.

EXAMPLE 7C

Synthesis of Lower Molecular Weight Copolyesters for Solventless Injections: PEDG/Cap 30/70 with N-methyldiethanolamine, NMDEA In this Example, a yet another diol was used, N-methyldiethanolamine, NMDEA. As with the use of DEG in Examples 3A and 3B, physical properties of the copolymer containing NMDEA instead of ethylene glycol in the structure were not altered significantly. Interestingly, we found in our laboratory that NMDEA monomer shows a relatively strong anti-bacterial activity for both gram-positive and gram-negative type. This may be a potentially useful feature.

A portion of the lower molecular weight Poly(ethylene diglycolate) (30 g) made as in Example 1 (IV=0.11 dL/g) was added into an oven dried 250 milliliter round bottom flask. In the nitrogen glove box, the e-caprolactone (70 g), an additional amount of NMDEA (2.95 mL) and catalyst, stannous octoate (0.030 mL) were charged. A mechanical stirrer, nitrogen adapter and stirrer bearing were added to the 250 ml flask's neck opening. The vessel was pulled under a vacuum of less than 250 mTorr at room temperature and held overnight. The next day the flask was released to nitrogen and placed in the oil bath. The bath temperature was set to 120° C. without agitation. Once the temperature reached approximately 95° C. the mechanical stirrer was set at 1 RPM. When the temperature reached 120° C., the oil bath setpoint was increased to 160° C. and the mixing was increased to 2 RPM. When the melt appeared homogenous and clear, the agitation was reduced to 1 RPM and the temperature was raised to 190° C. for 19 hours. After 19 hours the reaction was stopped and allowed to cool overnight under nitrogen.

All the glass inserts were removed from the flask, leaving only the mechanical stirrer, polymer resin and the round bottom flask. The polymer product was removed from the still hot reaction flask by pouring it directly into weighted Teflon coated pan. The pan was placed in the vacuum oven and kept under vacuum overnight. The next day the vacuum oven was set to 110° C. and the polymer was devolitized for 16 hours to remove residual monomers. The final copolyester is an amber, free flowing material at ambient conditions with the weight average molecular weight of 5,500 g/mol, and the melt viscosity of 24,000 cps as measured at 23° C.

EXAMPLE 7D

Synthesis of Lower Molecular Weight Copolyesters for Solventless Injections: PEDG/Cap 20/80 with Diethylene Glycol, DEG A portion of the lower molecular weight Poly(ethylene diglycolate) (20 g) made as in Example 1 (IV=0.11 dL/g) was added into an oven dried 250 milliliter round bottom flask. In the nitrogen glove box, the e-caprolactone (80 g), an additional amount of DEG (4.0 mL) and catalyst, stannous octoate (0.035 mL) were charged. A mechanical stirrer, nitrogen adapter and stirrer bearing were added to the 250 ml flask's neck opening. The vessel was pulled under a vacuum of less than 250 mTorr at room temperature and held overnight. The next day the flask was released to nitrogen and placed in the oil bath. The bath temperature was set to 120° C. without agitation. Once the temperature reached approximately 95° C. the mechanical stirrer was set at 1 RPM. When the temperature reached 120° C., the oil bath setpoint was increased to 160° C. and the mixing was increased to 2 RPM. When the melt appeared homogenous and clear, the agitation was reduced to 1.0 RPM and the temperature was raised to 190° C. for 19 hours. After 19 hours the reaction was stopped and allowed to cool overnight under nitrogen.

All the glass inserts were removed from the flask, leaving only the mechanical stirrer, polymer resin and the round bottom flask. The polymer product was removed from the still hot reaction flask by pouring it directly into weighted Teflon coated pan. The pan was placed in the vacuum oven and kept under vacuum overnight. The next day the vacuum oven was set to 110° C. and the polymer was devolitized for 16 hours to remove any residual monomers. The final copolyester is whitish, slurry material at ambient conditions with the weight average molecular weight of 5,400 g/mol, and the melt viscosity of 11,500 cps as measured at 23° C.

EXAMPLE 7E

Synthesis of Lower Molecular Weight Copolyesters for Solventless Injections: PEDG/Cap 25/75 with Quadrol A portion of the lower molecular weight Poly(ethylene diglycolate) (25 g) made as in Example 1 (IV=0.11 dL/g) was added into an oven dried 250 milliliter round bottom flask. In the nitrogen glove box, the e-caprolactone (75 g), an additional amount of Quadrol (5.0 mL) and catalyst, stannous octoate (0.033 mL) were charged. A mechanical stirrer, nitrogen adapter and stirrer bearing were added to the 250 ml flask's neck opening. The vessel was pulled under a vacuum of less than 250 mTorr at room temperature and held overnight. The next day the flask was released to nitrogen and placed in the oil bath. The bath temperature was set to 120° C. without agitation. Once the temperature reached approximately 95° C. the mechanical stirrer was set at 1 RPM. When the temperature reached 120° C., the oil bath setpoint was increased to 160° C. and the mixing was increased to 2 RPM. When the melt appeared homogenous and clear, the agitation was reduced to 1.0 RPM and the temperature was raised to 190° C. for 19 hours. After 19 hours the reaction was stopped and allowed to cool overnight under nitrogen.

All the glass inserts were removed from the flask, leaving only the mechanical stirrer, polymer resin and the round bottom flask. The polymer product was removed from the still hot reaction flask by pouring it directly into weighted Teflon coated pan. The pan was placed in the vacuum oven and kept under vacuum overnight. The next day the vacuum oven was set to 110° C. and the polymer was devolitized for 16 hours to remove any residual monomers. The final co-polyester is a slightly yellowish, free flowing material at ambient conditions with the melt viscosity of 44,000 cps as measured at 23° C.

TABLE 5

Selective examples of lower molecular weight PEDG/Cap copolymers

| Example | Polymer | Mw (g/mol) | IV (dL/g) | Melt viscosity @ 23° C. (cps) |
|---|---|---|---|---|
| 7A | PEDG/Cap 40/60 | 4,500 | 0.23 | 31,000 |
| 7B | PEDG/Cap 30/70 | 4,800 | 0.24 | 20,000 |
| 7C | PEDG/Cap 30/70 | 5,500 | NA | 24,000 |
| 7D | PEDG/Cap 20/80 | 5,400 | NA | 11,500 |
| 7E | PEDG/Cap 25/75 | NA | NA | 44,000 |

II. Co-Polyesters and Methods Used For Adhesion Prevention

The co-polyester of this embodiment, described herein, has been found to have good adhesion prevention properties. In one embodiment, the co-polyester comprises the reaction product of a polycondensation polymer (i.e., polycondensation polyester) and at least one lactone, wherein the polycondensation polyester comprises the reaction product of diglycolic acid and/or a derivative thereof and ethylene glycol.

In another embodiment, the polycondensation polyester comprises the reaction product of diglycolic acid and/or a derivative thereof, up to about 25 mole percent of an aliphatic diacid based on the total moles of acid, and ethylene glycol. Specifically, the aliphatic diacid may be an aliphatic alpha-omega dicarboxylic acid, including but not limited to 3,6-dioxaoctanedioic acid, 3,6,9-trioxaundecanedioic acid, and combinations thereof.

The polycondensation polyester may be synthesized by conventional techniques using conventional processes. For example, in a condensation polymerization, diglycolic acid and ethylene glycol may be polymerized in the presence of a catalyst at elevated temperatures and reduced pressures. A variety of catalysts may be used, but organometallic compounds have been found to be useful.

The catalyst for the polycondensation step of the synthesis is preferably tin based, e.g., stannous octoate. The most desirable catalyst is dibutyltin oxide and is present in the diglycolic acid/ethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 180° C., under an inert atmosphere until esterification of diglycolic acid is complete. Preferably, 165° C. has been found to be a desirable reaction temperature when employing a vertically stirred reactor. It should be noted that the optimum reaction temperature may be reactor and catalyst level dependent but can be found by one having only ordinary skill through the use of experiments. The first stage of the polycondensation reaction (inert gas at atmospheric pressure) is followed by polymerization under reduced pressure until the desired molecular weight and viscosity are achieved.

The weight average molecular weight of the polycondensation polymer can range from about 5,000 to about 30,000 g/mol, preferably from about 7,000 to about 20,000 g/mol, most preferably about 10,000 g/mol. This corresponds to an inherent viscosity range from about 0.25 to about 0.60 dL/g.

When the molecular weight of the polycondensation polymer is lower than about 5,000 g/mol, the molecular weight of the final co-polyester is too low to achieve the desired mechanical properties necessary for many medical device applications. Although molecular weight can be increased with increasing reaction time, it becomes increasingly difficult to achieve very high molecular weight. We have found, in general, that a molecular weight of the polycondensation polymer greater than about 30,000 g/mol, is not necessary to achieve desirable properties. One could however envision that this value is not an absolute bar. One might for instance, increase the molecular weight of the polycondensation polymer, and lower the amount of the lactone component used in the preparation of the final co-polyester.

The amount of polycondensation polyester used to prepare the co-polyester is about 40 to 50% by weight based on the total weight of the co-polyester.

Suitable lactone monomers include, but are not limited to, glycolide, lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations of two or more thereof. The preferred lactone monomer includes glycolide.

In one embodiment, the co-polyester may comprise the reaction product of a polycondensation polyester and a lactone such as glycolide.

In another embodiment, the co-polyester may comprise the reaction product of a polycondensation polyester and two or more lactones. For example, the co-polyester may comprise the reaction product of the polycondensation polyester, at least 75 mole percent glycolide based on the total moles of lactone, and a second lactone monomer.

The co-polyesters of this embodiment of the present invention may be conveniently synthesized by reaction of a dihydroxy poly(alkylene diglycolate) homopolymer or copolymer with a lactone by conventional techniques using conventional processes. For example, the polycondensation polyester is used as an α,ω-dihydroxy macroinitiator in a subsequent ring opening polymerization (ROP) with a lactone or a lactone mixture. The lactone monomers are copolymerized into the polycondensation polyester in the presence of a conventional organometallic catalyst at elevated temperatures. The catalyst for the ROP may be already present as residual catalyst in the polycondensation polyester or may be additional catalyst added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of lactone monomer-to-catalyst ranging from about 20,000/1 to infinity (i.e. no additional catalyst used). Thus one might utilize a tin-IV compound such as dibutyltin oxide at a diacid, for instance, diglycolic acid-to-catalyst ratio of about 10,000/1 to prepare the polycondensation polyester and then add a tin-II compound such as stannous octoate at a lactone-to-added-catalyst molar ratio of about 240,000/1 at the time of the ring opening polymerization. The co-polyesters of this embodiment of the present invention may be synthesized alternately with no additional catalyst being added at the time of the ROP as described in Example 10A.

The ROP step can be immediately conducted in the same reactor as that used to synthesize the polycondensation polyester immediately after the completion of the polycondensation step, if the reactor can provide adequate heat transfer and agitation. The lactone or lactone mixture can be added as a solid, a slurry, or in molten form. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. In the case of adding glycolide monomer, the monomer can be added as a solid. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the co-polyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 210° C. being a most preferred temperature, and held there for typically 2 hours. The exact reaction conditions will depend on the catalyst and its level; final reaction temperatures can vary from about 195° C. to 235° C., and more preferably from about 200° C. to about 220° C. Reaction times can vary from about 30 minutes to a few hours, depending on the catalyst and it level, and is typically conducted until the desired conversion of monomer to polymer is achieved.

An alternate reaction scheme that has been employed to prepare the co-polyesters of this embodiment of the invention has involved adding the lactone as a molten stream into the reactor. Thus the polycondensation polyester is added first, typically as a molten stream and the reactor evacuated. The reactor is heated to 130° C. Molten glycolide (or other glycolide rich mixture) at a temperature of 100° C. is added to the reactor. Although the batch temperature drops slightly, it is quickly brought back up to 130° C. at which point mixing is started. At this point, the process that was described above is followed.

Under the above described conditions, the co-polyesters of polycondensation polyester and lactones, will typically have a weight average molecular weight of about 10,000 g/mol (a.k.a. Daltons) to about 100,000 g/mol, preferably about 15,000 g/mol to about 50,000 g/mol, and more preferably about 20,000 g/mol to about 40,000 g/mol, most preferably about 30,000 g/mol. These molecular weights are sufficient to provide an effective inherent viscosity, typically between about 0.30 to about 2.0 deciliters per gram (dL/g), preferably about 0.40 to about 1.0 dL/g, more preferably about 0.50 to about 0.8 dL/g and most preferably about 0.65 dL/g, as measured in a 0.1 g/dL solution of hexafluoroisopropanol (HFIP) at 25° C.

The co-polyester may be applied directly to a surgical wound site or trauma site. For example ultra-thin films of about 1 to about 1000 microns can be applied to tissue surfaces, including the lumen of tissue such as a blood vessel, or particularly over tissue that has been sutured or repaired with a mesh. Once applied, the films are useful in the treatment or prevention of adhesions. Alternatively, articles such as medical devices may be molded from the co-polyester described herein by various conventional injection and extrusion molding processes. For example, the co-polyester may be molded to form films which, when sterilized by gamma or e-beam sterilization (i.e. between 15 to 40 kGy), suffer no detrimental effect to the physical properties and are useful as adhesion prevention barriers. Alternatively, the co-polyester may be a component of a medical device, i.e., the co-polyester may form one layer of a multi-laminate hernia repair mesh, or may be suspended in a polymer solution and coated onto at least a portion of a medical device.

EXAMPLES

Example 8A and 8B provides a detailed description of the synthesis of a α,ω-dihydroxy poly(ethylene diglycolate) homopolymer with different molecular weights. Examples 9A, 9C and 10A provide a detailed description of the reaction of α,ω-dihydroxy poly(ethylene diglycolate) homopolymer from Example 8A, with a lactone monomer, glycolide, to produce a co-polyester of the present invention. Example 9A details the preparation of a co-polyester of the present invention, an amorphous 40/60 (weight basis) poly(ethylene diglycolate-co-glycolate) co-polyester. The combined sources of tin in Example 9A result in a lactone-to-total-tin-catalyst ratio of about 19,250/1; the total tin in the final co-polyester is about 32 ppm on a weight basis. Example 9B provide a detailed description of the reaction of α,ω-dihydroxy poly(ethylene diglycolate) homopolymer from Example 8B, with a lactone monomer, glycolide, to produce a co-polyester of the present invention.

EXAMPLE 8A

Synthesis of Hydroxy Terminated Poly(Ethylene Diglycolate) Polycondensation Polyester A twin-agitated reactor with intermeshing HELICONE patterned blades (Atlantic 10CV reactor) was employed. After charging the reactor with 10.0 kg of diglycolic acid, 13.9 kg of ethylene glycol (EG) and 1.86 grams of dibutyltin oxide catalyst, the pressure was reduced to below 1 Torr and the vacuum preserved over night. The next day vacuum was released by introducing dry nitrogen (argon can be substituted) and heating of the mixture was started. When the reactor temperature reached 150° C., the agitator speed was set to 30 RPM. Soon, a first distillate containing mostly water, an esterification by-product, appeared. The reaction was continued at 165° C. for about 2 hours until approximately all water was distilled and/or first traces of EG appeared in the distillate. After the first nitrogen/argon stage was completed, pressure was lowered gradually to full vacuum while the temperature of the batch was maintained at 165° C. A vacuum of about 30-50 mTorr was maintained throughout the rest of the reaction. Melt and solution viscosities were regularly checked to ensure a polycondensation polyester of a desired molecular weight. A hydroxy end-capped polycondensation polyester was discharged after 75 hours of reaction time under vacuum. It was a fully amorphous, colorless viscous liquid with a glass transition temperature of about 3° C. Weight average molecular weight was 12,000 g/mol; the polycondensation polyester exhibited an inherent viscosity (IV) of 0.35 dL/g, as determined in HFIP at 25° C. at a concentration of 0.1 g/dL.

EXAMPLE 8B

Synthesis of Hydroxy Terminated Poly(Ethylene Diglycolate) Polycondensation Polyester A twin-agitated reactor with intermeshing HELICONE patterned blades (Atlantic 10CV reactor) was employed. After charging the reactor with 10.0 kg of diglycolic acid, 13.9 kg of ethylene glycol (EG) and 1.86 grams of dibutyltin oxide catalyst, the pressure was reduced to below 1 Torr and the vacuum preserved over night. The next day vacuum was released by introducing dry nitrogen (argon can be substituted) and heating of the mixture was started. When the reactor temperature reached 150° C., the agitator speed was set to 30 RPM. Soon first distillate appeared containing mostly water, an esterification by-product. The reaction was continued at 165° C. for about 2 hours until approximately all water was distilled and/or first traces of EG appeared in the distillate. After the first nitrogen/argon stage was completed, pressure was lowered gradually to full vacuum while the temperature of the batch was maintained at 165° C. A vacuum of about 30-50 mTorr was maintained throughout the rest of the reaction. Melt and solution viscosities were regularly checked to ensure a polycondensation polyester of a desired molecular weight. A hydroxy end-capped polycondensation polyester was discharged after 100 hours of reaction time under vacuum. It was a fully amorphous, colorless viscous liquid with a glass transition temperature of about 8° C. Weight average molecular weight was about 20,000 g/mol; the resin exhibited an inherent viscosity (IV) of 0.55 dL/g, as determined in HFIP at 25° C. at a concentration of 0.1 g/dL.

EXAMPLE 9A

The Copolymerization of an α,ω-Dihydroxy Poly(Ethylene Diglycolate) Homopolymer with a Lactone Monomer, Glycolide A portion of the polycondensation polyester (2.5 kg) produced in Example 8A was added into an Atlantic 8CV reactor, which is equipped with a melt tank reservoir allowing molten glycolide monomer (3.8 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components before the addition of catalyst, stannous octoate (0.412 ml of toluene solution, glycolide to catalyst level 240,000:1). The temperature was then increased to 210° C. and the reaction was continued for another two hours. The discharged co-polyester was fully amorphous, with a colorless to slightly yellow tint, and had a glass transition temperature of 23° C. Weight average molecular weight was 27,000 g/mol and an inherent viscosity of 0.64 dL/g, as determined in HFIP at 25° C. at a concentration of 0.1 g/dL, was recorded. The composition was confirmed by NMR to be 40/60 by weight poly-ethylene diglycolate-co-glycolide).

The co-polyester was made into 5 mil thick films via compression molding and then subject to gamma sterilization at 15, 30 and 38 kGy or e-beam sterilization at 25 kGy). No detrimental effect to the physical properties was observed.

EXAMPLE 9B

The Copolymerization of an α,ω-Dihydroxy Poly(Ethylene Diglycolate) Homopolymer with a Lactone Monomer, Glycolide A portion of the polycondensation polyester (2.5 kg) produced in Example 8B was added into an Atlantic 8CV reactor, which is equipped with a melt tank reservoir allowing molten glycolide monomer (2.5 kg) to be added later in a liquid state.

After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components before the addition of catalyst, stannous octoate (0.412 ml of toluene solution, glycolide to catalyst level 240,000:1). The temperature was then increased to 210° C. and the reaction was continued for another two hours. The discharged co-polyester was fully amorphous, with a colorless to slightly yellow tint, and had a glass transition temperature of 22° C. Weight average molecular weight was 36,000 g/mol and an inherent viscosity of 0.81 dL/g, as determined in HFIP at 25° C. at a concentration of 0.1 g/dL, was recorded. The composition was confirmed by NMR to be 50/50 by weight poly (ethylene diglycolate-co-glycolide).

EXAMPLE 9C

The Copolymerization of an α,ω-Dihydroxy Poly(Ethylene Diglycolate) Homopolymer with a Lactone Monomer, Glycolide A portion of the polycondensation polyester (2.5 kg) produced in Example 8A was added into an Atlantic 8CV reactor, which is equipped with a melt tank reservoir allowing molten glycolide monomer (2.5 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components before the addition of catalyst, stannous octoate (0.412 ml of toluene solution, glycolide to catalyst level 240,000:1). The temperature was then increased to 210° C. and the reaction was continued for another two hours. The discharged co-polyester was fully amorphous, with a colorless to slightly yellow tint, and had a glass transition temperature of 19° C. Weight average molecular weight was 22,000 g/mol and an inherent viscosity of 0.53 dL/g, as determined in HFIP at 25° C. at a concentration of 0.1 g/dL, was recorded. The composition was confirmed by NMR to be 50/50 by weight poly (ethylene diglycolate-co-glycolide).

EXAMPLE 10A

The Copolymerization of an α,ω-Dihydroxy Poly(Ethylene Diglycolate) Homopolymer with a Lactone Monomer, Glycolide The following example is similar to the Example 9A with a noted exception that additional catalyst was not added for the ring-opening portion of the synthesis and the reaction was conducted for a longer period of time. A portion of the polycondensation polyester (2.5 kg) produced in Example 8A was added into an Atlantic 8CV reactor, which is equipped with a melt tank reservoir allowing molten glycolide monomer (3.8 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components; no additional catalyst, (e.g. stannous octoate) was added for conducting this second step, ring opening polymerization. As exemplified herein, the lactone-to-added-catalyst molar ratio was then ∞/1, the lactone-to-total-tin-catalyst ratio was about 20,900/1; the total tin in the final co-polyester was about 29.5 ppm on a weight basis. The temperature was then increased to 210° C. and the reaction was continued for another three hours. The discharged co-polyester was fully amorphous, with a colorless to slightly yellow tint, and had a glass transition temperature of 23° C. Weight average molecular weight was 25,000 g/mol and an inherent viscosity of 0.65 dL/g, as determined in HFIP at 25° C. at a concentration of 0.1 g/dL, was recorded. Composition was confirmed by NMR to be 40/60 by weight poly(ethylene diglycolate-co-glycolide).

EXAMPLE 11

Two-Week Study Using an In Vivo Rabbit Hernia Sidewall Model

Animal Preparation:

The rabbits (Female, New Zealand White Rabbits, weights of approximately 3.5-5.5 kg) were fasted overnight prior to implantation. Elizabethan Collars were placed on the animals for approximately seven days post-surgery. An electric animal clipper equipped with a size 40 blade was used to depilate the surgical site. The area was vacuumed to remove clippings. The anesthetized animal was delivered to the operating table and placed in dorsal recumbency. The surgical site was prepared by wiping with alcohol followed by a surgical scrub solution (2% chlorhexidine acetate). A sterile surgical drape was then being applied to the prepared area using aseptic technique. Body weights was measured preoperatively and just prior to the end of the study.

Anesthesia:

On the day of surgery, each rabbit was pre medicated with glycopyrrolate (0.02 mg/kg, SC), approximately 15 minutes prior to anesthesia. Anesthesia was induced by using inhalation anesthesia (isoflurane at 5.0%) via facemask. Subsequent anesthesia was maintained with isoflurane (0.5-3.5% in 100% oxygen). Depth of anesthesia was monitored by heart rate and respiration as well as palpebral and paw pinch reflex, with anesthesia adjusted as needed. Intravenous access was established and Lactated Ringer's solution was administered at a rate of 11 ml/kg/hr throughout the surgical procedure.

Surgical Procedure:

A 12 cm (approximately) midline ventral abdominal incision was made approximately 4 cm caudal to the xiphoid cartilage. The cecum was exteriorized then abraded by wiping the surface ten times with a dry gauze sponge and turned 90 degrees and wiped again ten times. This procedure was continued until all aspects of the cecum had been abraded. A defect on each abdominal sidewall, approximately size 2×4.5 cm, was made lateral to and parallel with incision by sharp dissection. The defect was made approximately 2 cm lateral to the midline incision, and 3 cm caudal to the xiphoid process. A rectangular piece of control mesh fabricated from polypropylene fibers, and a composite fabricated from polypropylene mesh with a 5 mil film made from an amorphous 40/60 (weight basis) poly (ethylene diglycolate-co-glycolate) copolymer affixed to it, were sutured over each defect using a polypropylene suture (4-0) in a continuous pattern and oriented adjacent to the cecum. The abdominal wall was closed with a simple continuous suture pattern oversewn by several simple interrupted stitches using size 3-0 synthetic absorbable suture. Subcutaneous tissues were closed with a simple continuous suture pattern using size 3-0 synthetic absorbable suture. The skin was closed with stainless steel skin staples.

Euthanasia:

Animals were euthanized at 14 days postoperatively with an intravenous injection of Euthasol (or equivalent) at a dosage of 0.3 ml/kg of body weight. The medial ear vein was used for the injection site. Following administration of the drug, a stethoscope was used to confirm that there was no detectable cardiac and respiratory function. After death had been confirmed using a stethoscope, the femoral artery was transected as a redundant confirmation of death.

Necropsy:

Necropsy evaluation was performed, and macroscopic observations of all implant sites were recorded using the scoring scheme presented below. At the time of the macroscopic evaluation, the animals were identified such that the prosecutor scoring the adhesions was blinded to treatment. Macroscopic observations of implant sites were recorded according to the scheme presented below. The left and right sites were assessed separately. The presence and location of any extraneous adhesions were recorded.

Adhesion Extent Score:

Estimation of extent of adhesions to mesh surface:
0=no adhesions
1=1-25%
2=26-50%
3=51-75%
4=76-100%

Adhesion Severity Score:

Severity of most significant adhesions:
0=no adhesions
1=adhesion separated with minimal effort
2=adhesion separated with moderate effort
3=adhesion separated with difficulty Adhesion Total Score:

Total Score=Severity Score+Extent Score

Incidence:

Percentage of sites with adhesions

TABLE 6

14 Days Study Using an In Vivo Rabbit Abdominal Sidewall Model

|  | Polypropylene Mesh (PPM) Control | Composite of PPM/ 5 mil Co-polyester Film of Ex. 9A |
|---|---|---|
| Adhesion Extent Score | 1.6 | 0.5 |
| Adhesion Severity Score | 1.4 | 0.6 |
| Adhesion Total Score | 3.0 (out of 7) | 1.1 (out of 7) |
| Incidence | 75% | 38% |

In this study, the adhesion characteristics of a polypropylene-based mesh are compared to those of a composite of the same mesh top-coated with a film of the co-polyester of Example 9A, which is based on diglycolic acid with a crystallinity level of zero, i.e. fully amorphous. It is clear that in comparing the control (PPM) with the composition of the present invention that the adhesion performance of the latter is far superior. It should also be noted that the only adhesion found were at the perimeter of the device and can be attributed to the polypropylene sutures used to fix the device to the abdominal wall.

EXAMPLE 12

Applying the same methodology described in Example 11, but extending the Euthanasia time from 14 days to 3 month (i.e. animals were euthanized at 3 months postoperatively with an intravenous injection of Euthasol (or equivalent) at a dosage of 0.3 ml/kg of body weight). Adhesion prevention results are reported in Tables 7A and 7B.

TABLE 7A

3 Month Studies Using an In Vivo Rabbit Abdominal Sidewall Model

| Materials | Left Abdominal Defect | | | Right Abdominal Defect | | |
|---|---|---|---|---|---|---|
|  | Extent | Severity | Total | Extent | Severity | Total |
| Polypropylene Mesh (PPM) Control | 2 | 2 | 4 | 3 | 3 | 6 |
| Composite of PPM/5 mil Co-polyester Film of Ex. 9A | 0 | 0 | 0 | 0 | 0 | 0 |
| Composite of PPM/5 mil Co-polyester Film of Ex. 9C | 0 | 0 | 0 | 2 | 2 | 4 |
| Composite of PPM/5 mil Co-polyester Film of Ex. 9B | 1 | 1 | 2 | 0 | 0 | 0 |

Note:
Extent Score is out of 4, Severity Score is out of 3 and Total Score is out of 7.

TABLE 7B

Necropsy data of in-vivo abdominal wall rabbit study including several Co-polyester Formulations on Multiple Animals/Sites (5 Animals/10 sites/Article)

| Article | Composition | Incidence (%) | Severity | Comments |
|---|---|---|---|---|
| Control | Polypropylene Mesh | 80* | very strong adhesions, in 3 | due to strong adhesions the |

TABLE 7B-continued

Necropsy data of in-vivo abdominal wall rabbit study including several Co-polyester Formulations on Multiple Animals/Sites (5 Animals/10 sites/Article)

| Article | Composition | Incidence (%) | Severity | Comments |
|---|---|---|---|---|
| | (PPM) Control | | animals including multiple organs | defect's surface shrunk |
| A | Composite of PPM/5 mil Co-polyester Film of Ex. 9A sutured with polypropylene sutures | 40 | very weak adhesions (the lowest score overall), only one edge stronger with omentum | Only edge adhesions to omentum caused by suturing |
| B | Composite of PPM/5 mil Co-polyester Film of Ex. 9C sutured with polypropylene sutures | 60 | Edge adhesions of low intensity, 2 severe including multiple organs | some inflammation, free particles in the cavity, swelling |
| C | Composite of PPM/5 mil Co-polyester Film of Ex. 9B sutured with polypropylene sutures | 40 | all edge adhesions including one with cecum | 2 week study: no free particles in the cavity, large swelling |

Note:
*In two control animals, adhesions were extremely severe at one defect site including multiple organs, so that the other defect site was shielded and free of adhesions.

In this study, the adhesion characteristics of a polypropylene-based mesh, (PPM) are compared to those of a composite of the same mesh laminated with a 5 mil film of the co-polyesters of Examples 9A, 9B and 9C. It is clear in comparing the PPM control with the composition of the present invention, that the adhesion performance of the latter is far superior. It should also be noted that the only adhesion found were at the parameter of the device and can be attributed to the polypropylene sutures used to fix the device to the abdominal wall.

Although this invention has been shown and described with respect to detailed embodiments thereof, it will understood by those skilled in the art that various changes in form and detail thereof may be made without departing from the spirit and scope of the claimed invention.

What is claimed is:

1. A method of filling soft tissue, comprising:
   administering to a face of a patient or contouring a body of a patient with a composition comprising:
   a co-polyester which includes the reaction product of a polycondensation polyester and monomeric epsilon-caprolactone, wherein the polycondensation polyester comprises the reaction product of diglycolic acid and/or a derivative thereof and a diol, the co-polyester including about 50 to about 80% by weight of the epsilon-caprolactone, based on the total weight of the co-polyester.

2. The method according to claim 1, in which said composition is applied as a facial cosmetic or administered in lip augmentation, lip reconstruction, or reconstructive surgery, wherein the co-polyester is injected into the subcutaneous layer of the skin.

3. A process for preparing a co-polyester comprising:
   a. reacting diglycolic acid and/or a derivative thereof with a diol to produce a dihydroxy poly (alkylene diglycolate) and/or a dihydroxy poly (diol diglycolate); and
   b. reacting a dihydroxy poly (alkylene diglycolate) and/or a dihydroxy poly (diol diglycolate) homopolymer with monomeric epsilon-caprolactone to produce the co-polyester which includes about 50 to about 80% by weight of the epsilon-caprolactone, based on the total weight of the co-polyester.

4. The process according to claim 3, wherein the derivative of the diglycolic acid is 3,6-dioxaoctanedioic acid, 3,6,9-trioxaundecanedioic acid, or a combination thereof.

5. The process according to claim 3 wherein the diol is ethylene glycol, diethylene glycol (DEG), or N-methyldiethanolamine (NMDEA).

6. A process for preparing a co-polyester having weight average molecular weight of about 3,000 to about 10,000, comprising:
   a. reacting diglycolic acid and/or a derivative thereof with ethylene glycol to produce poly(ethylene diglycolate) (PEDG), or reacting diglycolic acid with diethylene glycol to produce poly(ethoxy ethylene) diglycolate (PEEDG), the PEDG or PEEDG having weight average molecular weight of from about 1,000 to about 2,000 g/mol;
   b. reacting the PEDG or PEEDG with an alcohol and monomeric epsilon-caprolactone to produce the co-polyester.

7. The process according to claim 6, wherein the derivative of the diglycolic acid is 3,6-dioxaoctanedioic acid, 3,6,9-trioxaundecanedioic acid or a combination thereof.

8. The process according to claim 6, wherein the alcohol is diethylene glycol (DEG), N-methyldiethanolamine (NMDEA) or a mulithydroxyl alcohol.

9. The process according to claim 8, wherein the mulithydroxyl alcohol is N,N,N',N'-tetra(2-hydroxypropyl)ethylene diamine.

* * * * *